(12) United States Patent
Persechini

(10) Patent No.: US 6,376,257 B1
(45) Date of Patent: Apr. 23, 2002

(54) DETECTION BY FRET CHANGES OF LIGAND BINDING BY GFP FUSION PROTEINS

(75) Inventor: Anthony Persechini, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 08/842,322

(22) Filed: Apr. 24, 1997

(51) Int. Cl.$^7$ ............... G01N 33/566; G01N 33/567
(52) U.S. Cl. ............... 436/501; 436/503; 436/536
(58) Field of Search ............... 436/536, 501, 436/503

(56) References Cited

U.S. PATENT DOCUMENTS 5,491,084 A    2/1996   Chalfie et al.

FOREIGN PATENT DOCUMENTS

WO    WO 96/23898    8/1996

OTHER PUBLICATIONS

Miyawaki et al, Nature, vol. 388, (Aug. 28, 1997), pp. 882–87.*
Romosen et al, The Journal of Biol. Chem., vol. 272(1), (May 16, 1997), pp. 13270–274.*
Mitra et al., "Fluorescence Resonance Energy Transfer Between Blue–Emitting and Red–Shifted Excitation Derivatives of the Green Fluorescent Protein," *Gene*, 173:13–17 (1996).
Crameri et al., "Improved Green Fluorescent Protein by Molecular Evolution Using DNA Shuffling,"*Nature Biotechnol.*, 14:315–319 (1996).
Cubitt et al., Understanding, Improving and Using Green Fluorescent Proteins,*TIBS*, 20:448–455 (1995).
Delagrave et al., Red–Shifted Excitation Mutants of the Green Fluorescent Protein,*Biotechnol.*, 13:151–154 (1995).
Gura, "Structure of Gene–Tag Protein Solved," *Science*, 273:1336 (1996).
Inouye et al., "Expression of the Gene and Fluorescence Characteristics of the Recombinant Protein," *FEBS Letters*, 341:277–280 (1994).
Marshall et al., "The Jellyfish Green Fluorescent Protein: A New Tool for Studying Ion Channel Expression and Function," *Neuron* , 14:211–215 (1995).
Ormo et al., "Crystal Structure of the *Aequorea victoria* Green Fluorescent Protein," *Science* 273:1392–1395 (1996).
Yang et al., "The Molecular Structure of Green Fluorescent Protein," *Nature Biotechnol.* 14:1246–1251 (1996).
Youvan et al., "Structure and Fluorescence Mechanism of GFP," Nature Biotechnol., 14:1219–1220 (1996).
Stull et al., "Phosphorylation of Myosin Light Chain Kinase: A Cellular Mechanism for $Ca^{2+}$ Desensitization," *Molecular and Cellular Biochem*, 127/128:229–337 (1993).

(List continued on next page.)

\* cited by examiner

*Primary Examiner*—Jyothsna Venkat
*Assistant Examiner*—Thomas Prasthofer
(74) *Attorney, Agent, or Firm*—Nixon Peabody LLP

(57) ABSTRACT

A method of monitoring the amount of primary or secondary ligand in a cell, using a green fluorescent protein complex and fluorescence resonance energy transfer between two GFP molecules to monitor the primary or secondary ligand, is disclosed. Further disclosed is a method of screening a molecule, such as a peptide, for primary ligand-binding activity, which also uses a green fluorescent protein complex and fluorescence resonance energy transfer between two GFP molecules, to screen the molecule or peptide. A green fluorescent protein complex having a first green fluorescent protein, a primary ligand-binding peptide, and a second green fluorescent protein, is also disclosed.

33 Claims, 7 Drawing Sheets

OTHER PUBLICATIONS

Cormack et al., "FACS–Optimized Mutants of the Green Fluorescent Protein (GFP), SSDI, pp. 33–38 (1996).

Persechini et al., "Different Mechanisms for $Ca^{2+}$ Dissociation from Complexes of Calmodulin with Nitric Oxide Synthase or Myosin Light Chain Kinase," J Biol. Chem., 271(1):62–67 (1996).

Crivici et al., "Molecular and Structural Basis of Target Recognition By Calmodulin," Ann. Rev. Biophys. Biomol. Struct., 24:85–116 (1995).

Chemical Abstracts, 127(5) Abstract No. 62698, XP002074734, (1997) see abstract, V.A. Romoser et al., "Detection in living cells of Ca 2+dependent changes in the fluorescent emission of an indicator composed of two green fluorescent protein varieants linked by a calmodulin–binding sequence. A new class of fluorescent indicators," *Journal of Biological Chemistry* 272(20):13270–13274 (1997).

Chemical Abstracts, 127(23) Abstract No. 316403, XP002074735, see abstract, Persechini et al., "Novel fluorescent indicator proteins for monitoring free intracellular Ca2+," *Cell Calcium* 22(3):209–216 (1997).

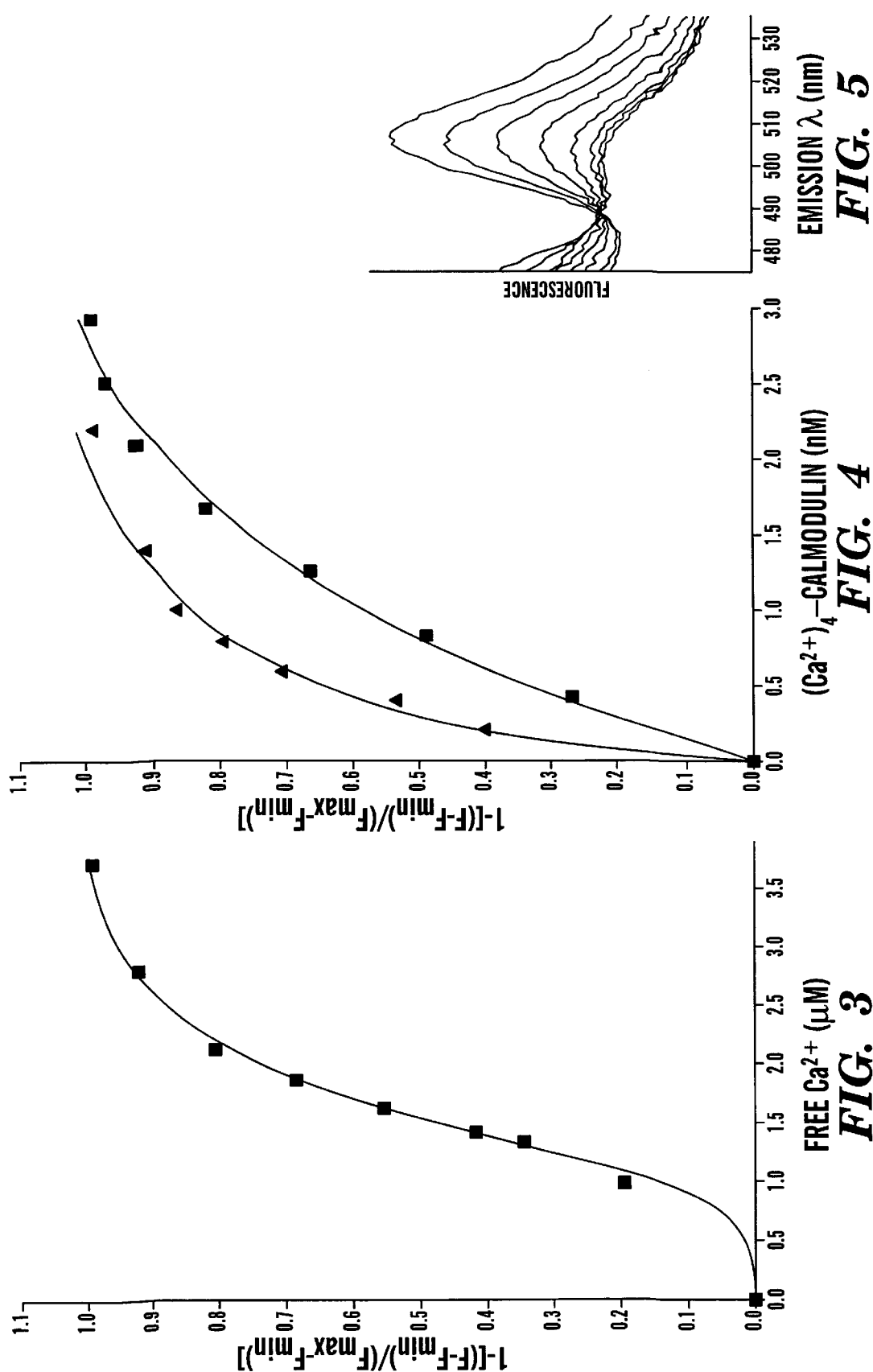

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 26 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

Gly Thr Ser Ser Arg Arg Lys Trp Asn Lys Thr Gly His Ala Val Arg
1               5                   10                  15

Ala Ile Gly Arg Leu Ser Ser Thr Gly Ala
            20                  25

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:2:

Gly Thr Ser Ser Gly Ser Ser Thr Thr Gly Ala
1               5                   10

(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

Ala Arg Arg Lys Trp Gln Lys Thr Gly His Ala Val Arg Ala Ile Gly
1               5                   10                  15

Arg Leu Ser Ser
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

Ala Arg Arg Lys Leu Lys Gly Ala Ile Leu Thr Thr Met Leu Ala Thr
1               5                   10                  15

Arg Asn Phe Ser
            20

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: Not Relevant (D) TOPOLOGY: linear (ii) MOLECULE TYPE: peptide (xi) SEQUENCE DESCRIPTION: SEQ ID NO:6:

Gly Val Arg Asn Ile Lys Ser Met Trp Glu Lys Gly Asn Val Phe Ser
1               5                   10                  15

Ser (2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

Ala Arg Arg Lys Leu Lys Ala Ala Val Lys Ala Val Val Ala Ser Ser
1               5                   10                  15

Arg Leu Gly Ser
            20

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Phe Met Asn Asn Trp Glu Val Tyr Lys Leu Leu Ala His Ile Arg Pro
1               5                   10                  15

Pro Ala Pro Lys Ser Gly Ser Tyr Thr Val
            20                  25

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

Ala Arg Lys Glu Val Ile Arg Asn Lys Ile Arg Ala Ile Gly Lys Met
1               5                   10                  15

Ala Arg Val Phe Ser Val Leu Arg
            20

(2) INFORMATION FOR SEQ ID NO:10:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

Leu Arg Arg Leu Ile Asp Ala Tyr Ala Phe Arg Ile Tyr Gly His Trp
1               5                   10                  15

Val Lys Lys Gly Gln Gln Gln Asn Arg Gly
                20                  25

(2) INFORMATION FOR SEQ ID NO:11:

(i) SEQUENCE CHARACTERISTICS:
            (A) LENGTH: 27 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:11:

Arg Gly Lys Phe Lys Val Ile Cys Leu Thr Val Leu Ala Ser Val Arg
1               5                   10                  15

Ile Tyr Tyr Gln Tyr Arg Arg Val Lys Pro Gly
                20                  25

(2) INFORMATION FOR SEQ ID NO:12:

(i) SEQUENCE CHARACTERISTICS:
            (A) LENGTH: 28 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:12:

Leu Arg Arg Gly Gln Ile Leu Trp Phe Arg Gly Leu Asn Arg Ile Gln
1               5                   10                  15

Thr Gln Ile Lys Val Val Asn Ala Phe Ser Ser Ser
                20                  25

(2) INFORMATION FOR SEQ ID NO:13:

(i) SEQUENCE CHARACTERISTICS:
            (A) LENGTH: 21 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:13:

Arg Arg Lys His Leu Gln Arg Pro Ile Phe Arg Leu Arg Cys Leu Val
1               5                   10                  15

Lys Gln Leu Glu Lys
                20

(2) INFORMATION FOR SEQ ID NO:14:

(i) SEQUENCE CHARACTERISTICS:
            (A) LENGTH: 21 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:14:

Thr Glu Lys Met Trp Gln Arg Leu Lys Gly Ile Leu Arg Cys Leu Val

```
                1               5                 10                15
Lys Gln Leu Glu Lys
                20

(2) INFORMATION FOR SEQ ID NO:15:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

Lys Arg Arg Ala Ile Gly Phe Lys Lys Leu Ala Glu Ala Val Lys Phe
1               5                 10                15
Ser Ala Lys Leu Met Gly Gln
                20

(2) INFORMATION FOR SEQ ID NO:16:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

Ile Lys Pro Ala Lys Arg Met Lys Phe Lys Thr Val Cys Tyr Leu Leu
1               5                 10                15
Val Gln Leu Met His Cys Arg Lys Met Phe Lys Ala
                20                  25

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:17:

Ile Asp Leu Leu Trp Lys Ile Ala Arg Ala Gly Ala Arg Ser Ala Val
1               5                 10                15
Gly Thr Glu Ala
                20

(2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:18:

Lys Ala His Lys Ala Ala Thr Lys Ile Gln Ala Ser Phe Arg Gly His
1               5                 10                15
Ile Thr Arg Lys Lys Leu Lys Gly Glu Lys Lys
```

```
                    20                  25

(2) INFORMATION FOR SEQ ID NO:19:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:19:

Lys Thr Ala Ser Pro Trp Lys Ser Ala Arg Leu Met Val His Thr Val
1               5                  10                  15

Ala Thr Phe Asn Ser Ile Lys Glu
            20

(2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:20:

Lys Lys Lys Lys Lys Arg Phe Ser Phe Lys Lys Ser Phe Lys Leu Ser
1               5                  10                  15

Gly Phe Ser Phe Lys Lys Ser Lys Lys
                20                  25

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:21:

Lys Lys Lys Lys Lys Phe Ser Phe Lys Lys Pro Phe Lys Leu Ser Gly
1               5                  10                  15

Leu Ser Phe Lys Arg Asn Arg Lys
            20

(2) INFORMATION FOR SEQ ID NO:22:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

Lys Gln Gln Lys Glu Lys Thr Arg Trp Leu Asn Thr Pro Asn Thr Tyr
1               5                  10                  15

Leu Arg Val Asn Val Ala Asp Glu Val Gln Arg Asn Met Gly Ser
            20                  25                  30
```

(2) INFORMATION FOR SEQ ID NO:23:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:23:

Lys Asp Gln Val Ala Asn Ser Ala Phe Gln Glu Arg Leu Arg Lys His
1               5                  10                  15

Gly Leu Glu Val Ile
            20

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Tyr His Arg Leu Arg Asp Leu Leu Leu Ile Val Lys Arg Ile Val Glu
1               5                  10                  15

Leu Leu Gly Arg Arg
            20

(2) INFORMATION FOR SEQ ID NO:25:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:25:

Gln Gln Leu Ala Thr Leu Ile Gln Lys Thr Tyr Arg Gly Trp Arg Cys
1               5                  10                  15

Arg Thr His Tyr Gln Leu Met
            20

(2) INFORMATION FOR SEQ ID NO:26:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:26:

Arg Ala Ala Cys Ile Arg Ile Gln Lys Thr Ile Arg Gly Trp Leu Leu
1               5                  10                  15

Arg Lys Arg Tyr Leu Cys Met Gln
            20

(2) INFORMATION FOR SEQ ID NO:27:

(i) SEQUENCE CHARACTERISTICS:

(A) LENGTH: 14 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:27:

Ile Asn Leu Lys Ala Leu Ala Ala Leu Ala Lys Lys Ile Leu
1               5                   10

(2) INFORMATION FOR SEQ ID NO:28:

(i) SEQUENCE CHARACTERISTICS:
            (A) LENGTH: 26 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:28:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

(2) INFORMATION FOR SEQ ID NO:29:

(i) SEQUENCE CHARACTERISTICS:
            (A) LENGTH: 30 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:29:

His Ser Gln Gly Thr Phe Thr Thr Ser Asp Tyr Ser Lys Tyr Leu Asp
1               5                   10                  15

Ser Arg Arg Ala Gln Asp Phe Val Gln Trp Leu Met Asn Thr
                20                  25                  30

(2) INFORMATION FOR SEQ ID NO:30:

(i) SEQUENCE CHARACTERISTICS:
            (A) LENGTH: 27 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:30:

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
                20                  25

(2) INFORMATION FOR SEQ ID NO:31:

(i) SEQUENCE CHARACTERISTICS:
            (A) LENGTH: 28 amino acids
            (B) TYPE: amino acid
            (C) STRANDEDNESS: Not Relevant
            (D) TOPOLOGY: linear (ii) MOLECULE TYPE: peptide -continued (xi) SEQUENCE DESCRIPTION: SEQ ID NO:31:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO:32:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:32:

Tyr Ala Asp Gly Thr Phe Ile Ser Asp Tyr Ser Ala Ile Met Asn Lys
1               5                   10                  15

Ile Arg Gln Gln Asp Phe Val Asn Trp Leu Leu Ala Gln Gln Gln Lys
            20                  25                  30

Ser (2) INFORMATION FOR SEQ ID NO:33:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:33:

Lys Leu Trp Lys Lys Leu Leu Lys Leu Leu Lys Lys Leu Leu Lys Leu
1               5                   10                  15

Gly

US 6,376,257 B1

DETECTION BY FRET CHANGES OF LIGAND BINDING BY GFP FUSION PROTEINS

The subject matter of this application was made with support from the United States Government under grant no. DK44322-03 of the National Institutes of Health.

FIELD OF THE INVENTION

The present invention relates generally to cell monitoring and ligand detection and evaluation, and more particularly to a method of monitoring the level of a primary ligand in a cell or a method of evaluating a molecule for primary ligand-binding activity, using a green fluorescent protein fusion complex that exhibits ligand-dependent fluorescence resonance energy transfer.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The activity of a cell is influenced and regulated by many molecules. Many cells have receptors which activate pathways within the cell, such as the cAMP pathway or the phosphoinositide pathway. Such receptors are often activated by a ligand. When the ligand binds to its receptor, the receptor activates the pathway. Other molecules influential in a cell include ions such as calcium ions. In an attempt to understand the molecular biology of a cell, the ways in which cells interact, or even causes of cell death, more knowledge is continually needed regarding the distribution and/or pattern of expression of various molecules within a cell or within a tissue or organ.

One example of such a molecule is calmodulin. Calmodulin modulates the activities of a large and constantly increasing number of known target proteins (Bredt and Snyder 1990; Cho et al. 1992; Edelman et al. 1996; Crivici and Ikura 1995; Kink et al. 1990; Lu and Means 1993; Manalan and Klee 1984; Means et al. 1991; Wang et al. 1996). Through their actions it participates in the regulation of most processes in the cell including motility, axonal transport, synaptic transmission, ion homeostasis, cell cycle progression, gene expression and apoptosis. It is of interest to determine whether maximal and resting free $(Ca^{2+})_4$-calmodulin levels vary among cell types, or at different points in the cell cycle, which has been shown to be associated with cyclic changes in total calmodulin levels. It would also be of interest to investigate spatio-temporal changes in calmodulin activity during cellular events that involve it.

It would also be of interest to determine maximal and resting levels of other molecules and ligands, in various cell types, or at different points in the cell cycle, and well as to determine spatio-temporal changes in ligand-binding activity during cellular events that involve it.

SUMMARY OF INVENTION

To this end, the subject invention provides a method of monitoring the amount of a primary or secondary ligand in a cell. The method first involves the construction of a green fluorescent protein (GFP) complex. The green fluorescent protein complex comprises a first green fluorescent protein which is excited at a first wavelength and which emits fluorescence at a second wavelength; a primary ligand-binding peptide having an amino terminal end and a carboxy terminal end, the amino terminal end of the primary ligand-binding peptide being covalently attached to the first green fluorescent protein; and a second green fluorescent protein which is excited at the second wavelength and which emits fluorescence at a third wavelength, the carboxy terminal end of the primary ligand-binding peptide being covalently attached to the second green fluorescent protein. The constructed green fluorescent protein complex is then introduced into a cell, and a base amount of fluorescence emission at the third wavelength when the cell is excited at the first wavelength is determined. This determination provides a control or base amount of fluorescence resonance energy transfer between the two green fluorescent proteins of the green fluorescent protein complex. The amount of fluorescence emission over time at the third wavelength when the cell is excited over time at the first wavelength is determined. Next, a comparison is made of the amount of fluorescence emission over time to the base amount of fluorescence emission, wherein an amount of fluorescence emission less than the base amount of fluorescence emission indicates an increase in the amount of the primary ligand in the cell. In particular, the primary ligand present in the cell has bound to the primary ligand-binding peptide, changing the distance between the two GFP molecules and altering fluorescence resonance energy transfer (FRET) between them. Changes in the amount of fluorescence emission over time can be used to monitor changes in the amount of the primary ligand in the cell over time.

By quantitating the amount of fluorescence emission over time using the subject method, one can estimate the amount of the primary ligand in the cell over time.

The subject invention further provides a method for monitoring the amount of a secondary ligand in the cell, wherein the secondary ligand binds to the primary ligand and is necessary for binding of the primary ligand to the primary ligand-binding peptide. This method is as recited above, except the method further comprises introducing a known concentration of the primary ligand into the cell prior to determining the base amount of fluorescence emission. When the amount of fluorescence emission is less than the base amount of fluorescence emission, it is an indication of the presence of the secondary ligand. As above, changes in the amount of fluorescence emission over time indicate changes in the amount of the secondary ligand in the cell over time.

The invention further provides a method of screening a peptide for primary ligand-binding activity. The method comprises constructing a green fluorescent protein complex. In this embodiment, the green fluorescent protein complex comprises the first green fluorescent protein and the second green fluorescent protein as described above, but they are covalently attached by a peptide having an amino terminal end and a carboxy terminal end, the amino terminal end of the peptide being covalently attached to the first green fluorescent protein and the carboxy terminal end of the peptide being covalently attached to the second green fluorescent protein. The green fluorescent protein complex is introduced into a cell in the absence of the primary ligand, and a determination of the base amount of fluorescence emission at the third wavelength is made when the cell is excited at the first wavelength. The candidate primary ligand is then added to the cell, and a determination of the amount of fluorescence emission at the third wavelength is made when the cell is excited at the first wavelength. A comparison is then made of the amount of fluorescence emission to the base amount of fluorescence emission, wherein an amount of fluorescence emission less than the base amount of fluorescence emission indicates that the molecule has primary ligand-binding activity. Alternatively, this method of screening a peptide for primary ligand-binding activity can be performed in vitro in, for example, a test tube or well. The green fluorescent protein complex is expressed in a cell and then purified from the cell by conventional protein purification techniques (such as affinity chromatography). The purified protein complex is placed in a test tube or well and a determination is made of the base amount of fluorescence emission at the third wavelength when the purified protein complex is excited at the first wavelength. The candidate primary ligand is then added to the test tube or well, and a determination is made of the amount of fluorescence emission at the third wavelength when the purified protein complex (in the presence of purified primary ligand) is excited at the first wavelength. As in the previous embodiment, a comparison is then made of the amount of fluorescence emission to the base amount of fluorescence emission, wherein an amount of fluorescence emission less than the base amount of fluorescence emission indicates that the peptide has primary ligand-binding activity.

Further provided is another method of screening a molecule for the ability to bind a primary ligand in competition with the primary ligand-binding peptide where the constructed green fluorescent protein complex comprises the first green fluorescent protein and the second green fluorescent protein covalently attached by a primary ligand-binding peptide having an amino terminal end and a carboxy terminal end. The amino terminal end of the primary ligand-binding peptide is covalently attached to the first green fluorescent protein and the carboxy terminal end of the primary ligand-binding peptide is covalently attached to the second green fluorescent protein. The green fluorescent protein complex is introduced into a cell or test vesicle (such as a test tube or test well) with the primary ligand, and a determination is made of the base amount of fluorescence emission at the third wavelength when the cell or contents of the test vesicle are excited at the first wavelength A molecule, such as a peptide, is then added to the cell or test vesicle, and a determination is made of the amount of fluorescence emission at the third wavelength when the cell or contents of the test vesicle is excited at the first wavelength. A comparison is then made of the amount of fluorescence emission to the base amount of fluorescence emission, wherein an amount of fluorescence emission greater than the base amount of fluorescence emission indicates that the molecule has primary ligand-binding activity. In particular, the molecule has bound the primary ligand thereby preventing the primary ligand from interfering with energy transfer between the two GFPs (the primary ligand does this by binding to the primary ligand-binding peptide that covalently attaches the two GFPs).

The invention further provides a green fluorescent protein complex which comprises a first green fluorescent protein which is excited at a first wavelength and which emits fluorescence at a second wavelength; a primary ligand-binding peptide which reversibly binds a primary ligand, the primary ligand-binding peptide having an amino terminal end and a carboxy terminal end, the amino terminal end of the primary ligand-binding peptide being covalently attached to the first green fluorescent protein; and a second green fluorescent protein which is excited at the second wavelength and which emits fluorescence at a third wavelength, the carboxy terminal end of the primary ligand-binding peptide being covalently attached to the second green fluorescent protein. When the green fluorescent protein complex is excited at the first wavelength, the amount of fluorescence emission at the third wavelength is reduced when the primary ligand-binding peptide is bound to primary ligand as compared to the amount of fluorescence emission at the third wavelength when the primary ligand-binding peptide is not bound to the primary ligand. Also provided is a cell which expresses the green fluorescent protein complex.

BRIEF DESCRIPTION OF THE DRAWINGS

These and other features and advantages of this invention will be evident from the following detailed description of preferred embodiments when read in conjunction with the accompanying drawings in which:

FIG. 3 characterizes the calmodulin binding by FIP-$CB_{SM}$, showing the titration of a mixture of 8.2 nM FIP-$CB_{SM}$ and 200 nM calmodulin with increasing concentrations of free $Ca^{2+}$ ion;

FIG. 4 characterizes the calmodulin binding by FIP-$CB_{SM}$, showing the binding of $(Ca^{2+})_4$-calmodulin to FIP-$CB_{SM}$ at concentrations of 1 (■) and 1.4 (▲) nM;

FIG. 5 shows the emission spectra for titration of FIP-$CB_{SM}$ at a 1.4 nM concentration;

DETAILED DESCRIPTION

Figure 1:
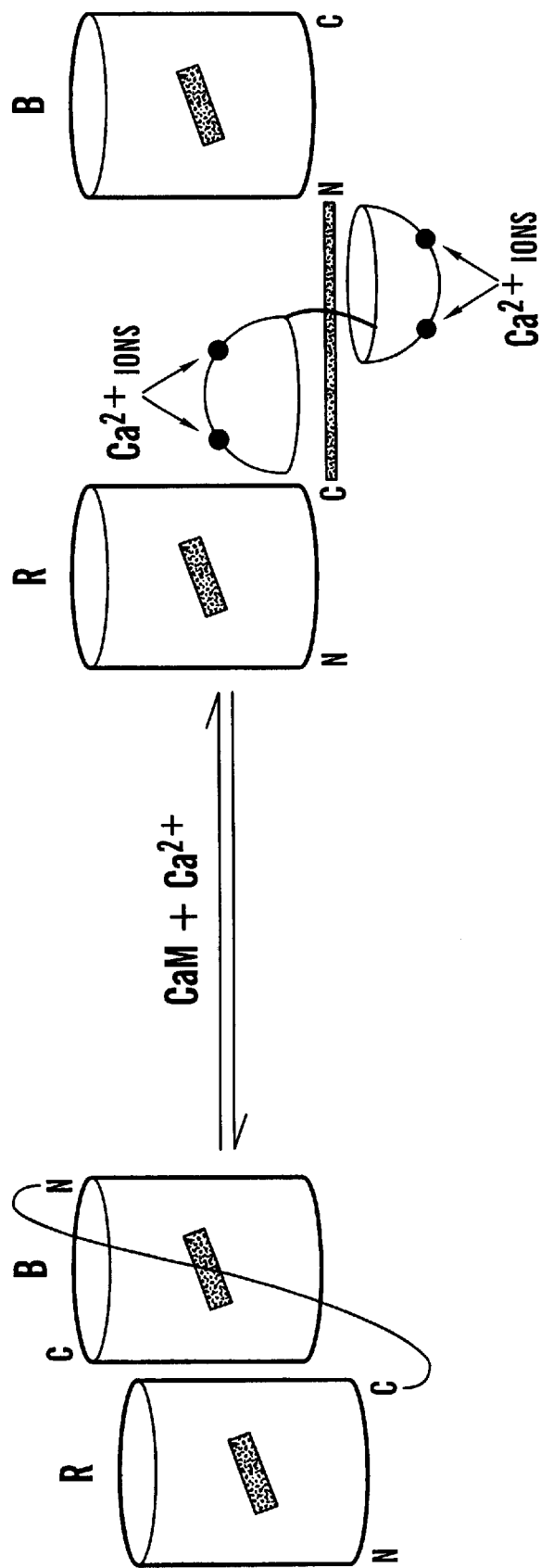
FIG. 1 illustrates the conformational change undergone by FIP-$CB_{SM}$ upon binding $(Ca^{2+})_4$-calmodulin.

The subject invention provides a method of monitoring the amount of a primary or secondary ligand in a cell. The method first involves the construction of a green fluorescent protein complex. The green fluorescent protein complex comprises a first green fluorescent protein which is excited at a first wavelength and which emits fluorescence at a second wavelength; a primary ligand-binding peptide having an amino terminal end and a carboxy terminal end, the amino terminal end of the primary ligand-binding peptide being covalently attached to the first green fluorescent protein; and a second green fluorescent protein which is excited at the second wavelength and which emits fluorescence at a third wavelength, the carboxy terminal end of the primary ligand-binding peptide being covalently attached to the second green fluorescent protein. The constructed green fluorescent protein complex is then introduced into a cell and a base amount of fluorescence emission at the third wavelength when the cell is excited at the first wavelength is determined. This determination provides a control or base amount of fluorescence resonance energy transfer between the two green fluorescent proteins of the green fluorescent protein complex. The amount of fluorescence emission over time at the third wavelength when the cell is excited over time at the first wavelength is determined. Next, a comparison is made of the amount of fluorescence emission over time to the base amount of fluorescence emission, wherein an amount of fluorescence emission less than the base amount of fluorescence emission indicates an increase in the amount of the primary ligand in the cell. Changes in the amount of fluorescence emission over time can be used to monitor changes in the amount of the primary ligand in the cell over time.

By quantitating the amount of fluorescence emission over time using the subject method, one can estimate the amount of the primary ligand in the cell over time.

As used herein, a primary ligand refers to any molecule binding directly to the primary ligand-binding peptide in the GFP complex. An example of a primary ligand in accordance with the subject invention is calmodulin (where the primary ligand-binding peptide is a calmodulin-binding peptide). Various calmodulin-binding peptides are known in the art and each can be used to tether the two green fluorescent proteins together. One calmodulin-binding peptide has the amino acid sequence as shown in SEQ ID NO:1. Examples of additional calmodulin-binding peptides are shown in Table 1 (see Crivici and Ikura 1995, and Persechini et al. 1996).

As further used herein, a green fluorescent protein refers to any fluorescent protein containing a naturally occurring fluorophore. The only requirement is that the two selected green fluorescent proteins have different excitation and fluorescence emission wavelengths. This is necessary to evaluate the fluorescence resonance energy transfer between the two proteins. Two examples of green fluorescent proteins which can be used in accordance with the subject invention are the red-shifted green fluorescent protein (which is excited at a wavelength maxima of 495 nm and emits fluorescence at a wavelength maxima of 505 nm) and the blue-shifted green fluorescent protein (which is excited at a wavelength maxima of 380 nm and emits fluorescence at a wavelength maxima of 440 nm). Other potentially suitable green fluorescent proteins include the GFP from *Aequorea victoria* (U.S. Pat. No. 5,491,084). A plasmid encoding the GFP of *Aequorea victoria* is available from the ATCC as Accession No. 75547. A mutated form of this GFP (a red-shifted mutant form) designated pRSGFP-C1 is commercially available from Clontech Laboratories, Inc. (Palo Alto, Calif.). For further discussions of various GFP molecules, see Crameri et al. 1996; Delegrave et al. 1995; Gura 1996; Inouye and Tsuji 1994; Marshall et al. 1995; Ormo et al. 1996; Yang et al. 1996; and Youvan and Michel-Beyerle 1996.

In the case of the primary ligand calmodulin, as with any other appropriate primary ligand, the binding of calmodulin by the calmodulin-binding peptide may be dependent on the presence of a secondary ligand which binds to the primary ligand. For example, calmodulin requires the presence of calcium ion in order to bind to the calmodulin-binding peptide having SEQ ID NO:1. In these cases, the method of the subject invention further comprises introducing into the cell the secondary ligand necessary for binding of the primary ligand to the primary ligand-binding peptide. The amount of the secondary ligand in the cell can thereby be monitored by introducing the primary ligand into the cell prior to determining the base amount of fluorescence emission. When the amount of fluorescence emission is less than the base amount of fluorescence emission, it is an indication of the presence of the secondary ligand in the cell. Furthermore, changes in the amount of fluorescence emission over time indicate changes in the amount of the secondary ligand in the cell over time. One embodiment of the subject invention thus provides for the monitoring of such secondary ligands within cells. This is very advantageous, especially for the monitoring of secondary ligands such as the calcium ion, because the level of calcium ion in a cell can be quantitated by indirect detection via the calcium ion's interaction with calmodulin and the calmodulin-binding peptide. In this embodiment, the primary ligand can be introduced into the cell by covalently attaching the primary ligand to one of the first green fluorescent protein or the second green fluorescent protein in the green fluorescent protein complex. This fixes the concentration of the primary ligand in relation to the indicator.

Other examples of secondary ligands in accordance with the subject invention include metal ions.

As used herein, covalent attachment refers to a non-reversible attachment whereas "bound" or "binding" refer to reversible attachments.

The invention further provides a method of screening a peptide for primary ligand-binding activity. The method comprises constructing a green fluorescent protein complex. In this embodiment, the green fluorescent protein complex comprises the first green fluorescent protein and the second green fluorescent protein as described above, but they are covalently attached by a peptide having an amino terminal end and a carboxy terminal end, the amino terminal end of the peptide being covalently attached to the first green fluorescent protein and the carboxy terminal end of the peptide being covalently attached to the second green fluorescent protein. The green fluorescent protein complex is introduced into a cell in the absence of the primary ligand, and a determination of the base amount of fluorescence emission at the third wavelength is made when the cell is excited at the first wavelength. The primary ligand is then added to the cell, and a determination of the amount of fluorescence emission at the third wavelength is made when the cell is excited at the first wavelength. A comparison is then made of the amount of fluorescence emission to the base amount of fluorescence emission, wherein an amount of fluorescence emission less than the base amount of fluorescence emission indicates that the peptide has primary ligand-binding activity. Preferably, the primary ligand is calmodulin. Alternatively, this method of screening a peptide for primary ligand-binding activity can be performed in vitro in, for example, a test tube or well. The green fluorescent protein complex is expressed in a cell and then purified from the cell by conventional protein purification techniques (such as affinity chromatography). The purified protein complex is placed in a test tube or well and a determination is made of the base amount of fluorescence emission at the third wavelength when the purified protein complex is excited at the first wavelength. Purified primary ligand is then added to the test tube or well, and a determination is made of the amount of fluorescence emission at the third wavelength when the purified protein complex (in the presence of purified primary ligand) is excited at the first wavelength. As in the previous embodiment, a comparison is then made of the amount of fluorescence emission to the base amount of fluorescence emission, wherein an amount of fluorescence emission less than the base amount of fluorescence emission indicates that the peptide has primary ligand-binding activity.

Further provided is a method of screening a molecule for the ability to bind a known primary ligand where the constructed green fluorescent protein complex comprises the first green fluorescent protein and the second green fluorescent protein covalently attached by a primary ligand-binding peptide having an amino terminal end and a carboxy terminal end. The amino terminal end of the primary ligand-binding peptide is covalently attached to the first green fluorescent protein and the carboxy terminal end of the primary ligand-binding peptide is covalently attached to the second green fluorescent protein. The green fluorescent protein complex is introduced into a cell or test vesicle with the primary ligand, and a determination is made of the base amount of fluorescence emission at the third wavelength when the cell or contents of the test vesicle is excited at the first wavelength. A molecule, such as a peptide, is then added to the cell or test vesicle, and a determination is made of the amount of fluorescence emission at the third wavelength when the cell or contents of the test vesicle is excited at the first wavelength. A comparison is then made of the amount of fluorescence emission to the base amount of fluorescence emission, wherein an amount of fluorescence emission greater than the base amount of fluorescence emission indicates that the molecule has primary ligand-binding activity. As above, preferably the primary ligand is calmodulin and the primary ligand-binding peptide (a calmodulin-binding peptide) has an amino acid sequence as shown in SEQ ID NO:1. This method of screening a molecule for the ability to bind a known primary ligand can also be performed in vitro in, for example, a test tube or well, as discussed above for the in vitro screening of a peptide for the ability to bind a known primary ligand.

The invention further provides a green fluorescent protein complex which comprises a first green fluorescent protein which is excited at a first wavelength and which emits fluorescence at a second wavelength; a primary ligand-binding peptide which reversibly binds a primary ligand, the primary ligand-binding peptide having an amino terminal end and a carboxy terminal end, the amino terminal end of the primary ligand-binding peptide being covalently attached to the first green fluorescent protein; and a second green fluorescent protein which is excited at the second wavelength and which emits fluorescence at a third wavelength, the carboxy terminal end of the primary ligand-binding peptide being covalently attached to the second green fluorescent protein. When the green fluorescent protein complex is excited at the first wavelength, the amount of fluorescence emission at the third wavelength is reduced when the primary ligand-binding peptide is bound to primary ligand as compared to the amount of fluorescence emission at the third wavelength when the primary ligand-binding peptide is not bound to the primary ligand. Also provided is a cell which expresses the green fluorescent protein complex. Suitable cells include bacterial and mammalian cells, including *Escherichia coli* cells.

Preferably, the primary ligand is calmodulin and the primary ligand-binding peptide is a calmodulin-binding peptide, such as the peptide having the amino acid sequence as shown in SEQ ID NO:1. The first green fluorescent protein is preferably a blue-shifted green fluorescent protein (which is excited at a first wavelength maxima of 380 nm and emits fluorescence at a second wavelength maxima of 440 nm and emits the second green fluorescent protein is preferably a red-shifted green fluorescent protein (which is excited at the second wavelength maxima of 495 nm and emits fluorescence at a third wavelength maxima of 505 nm). In one embodiment, the green fluorescent protein complex may further comprise the primary ligand covalently attached to one of the first green fluorescent protein or the second green fluorescent protein so as to provide for detection of a second ligand. Here the sensitivity of the indicator to the secondary ligand can be modified by altering the interface between the primary ligand and the primary ligand-binding peptide.

Standard techniques can be used to replace the GFPs of plasmid pFIP-CB$_{SM}$ with alternative GFPs, and standard techniques can be used to replace the calmodulin-binding peptide of plasmid pFIP-CB$_{SM}$ with alternative primary ligand-binding peptides (or a peptide to be screened for primary ligand-binding activity). Generally, this involves the use of restriction enzymes and ligation (see below).

The green fluorescent protein complex according to the subject invention can be introduced into a cell. Techniques for introducing the complex or a deoxyribonucleic acid molecule in the form of a plasmid allowing expression of the complex into a cell are known in the art. These include: 1) microinjection, in which the purified complex or RNA is injected directly into the cell through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus. Preferably, the plasmid is introduced into a cell by microinjection or the use of a vector (a plasmid or viral vector, for example). U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

The methods of the subject invention use fluorescence resonance energy transfer (FRET) between spectral variants of GFP to monitor primary ligands or secondary ligands. FRET is described in more detail in Mitra et al. 1996. Briefly, FRET is a process in which an excited fluorophore (the donor) transfers its excited state energy to a light absorbing molecule (the acceptor). Generally, the fluorescence of the donor decreases as the fluorescence of the acceptor increases and vice versa.

EXAMPLE I

The $Ca^{2+}$-binding protein, calmodulin, is a key transducer of intracellular $Ca^{2+}$ ion signals, mainly through $Ca^{2+}$-dependent modulation of numerous enzyme activities (Bredt and Snyder 1990; Cho et al. 1992; Edelman et al. 1996; Crivici and Ikura 1995; Kink et al. 1990; Lu and Means 1993; Manalan and Klee 1984; Means et al. 1991; Wang et al. 1996). This example describes a fluorescent indicator protein whose emission changes reversibly from green to blue light when it binds $(Ca^2)_4$-calmodulin ($K_d$=0.4 nM), in analogy with a calmodulin-dependent enzyme activity. This response has been monitored in cells microinjected with the indicator. It closely mirrors changes in the intracellular free $Ca^{2+}$ ion concentration, responding to a rapid, receptor-mediated, increase with no discernable lag (<300 ms). The fractional indicator response that can be achieved in the absence of co-injected calmodulin is consistent with a free intracellular $(Ca^{2+})_4$-calmodulin concentration of ~1 nM. Images using green/blue fluorescence ratios demonstrate the utility of this indicator for investigating spatio-temporal changes in $(Ca^{2+})_4$-calmodulin levels in living cells.

Figure 2:
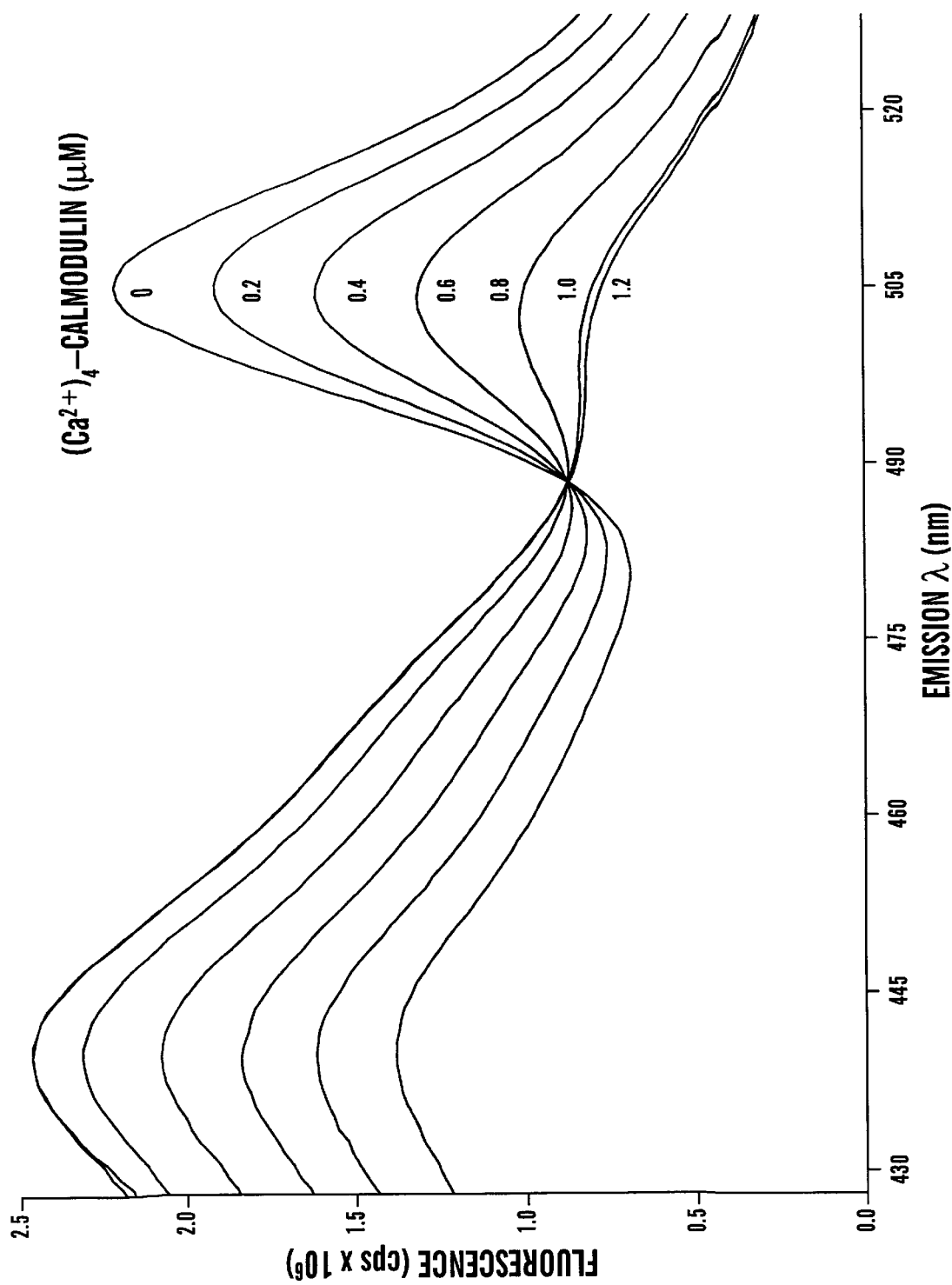
FIG. 2 illustrates the calmodulin-dependent changes in the FIP-$CB_{SM}$ fluorescence emission spectrum.

The fluorescent indicator protein (FIP-$CB_{SM}$) contains two previously characterized green fluorescent protein (GFP) variants; one with fluorescence excitation and emission maxima of ~380 and ~440 nm (BGFP; Heim et al. 1994), the other with excitation and emission maxima of ~495 and ~505 nm (RGFP; Delegrave et al. 1995). These are joined by a linker sequence containing the calmodulin-binding domain of avian smooth muscle myosin light chain kinase (FIG. 1). When excited at 380 nm, FIP-$CB_{SM}$ exhibits a pronounced emission peak at 505 nm, which is reduced by 65% when $Ca^{2+}$-calmodulin is bound to the linker. There is a corresponding increase in $F_{440}$ so that the $F_{440}/F_{505}$ emission ratio increases from a value of 0.6 to a value of 3 when FIP-$CB_{SM}$ is fully saturated with calmodulin. This behavior is consistent with a calmodulin-dependent reduction in FRET between the fluorophores in the two GFP domains in FIP-$CB_{SM}$ (FIG. 2). This is the first example of a fusion between two GFPs that exhibits reversible changes in inter-fluorophore FRET in response to a ligand. The fluorescence properties of FIP-$CB_{SM}$ make it suitable for single-wavelength and emission-ratio measurements. FIP-$CB_{SM}$ binds $(Ca^{2+})_4$-calmodulin with a $K_d$ of 0.4 nM, which is close to the 1 nM apparent value inferred for the complex between calmodulin and smooth muscle myosin light chain kinase (FIGS. 3 and 4)(Adelstein et al. 1981).

Purified GFP is known to dimerize in solution, and crystallographic data suggest that the two subunits are in an antiparallel orientation, placing the N-terminus of one protein about 70 Å from the C-terminus of the other (Ormo et al. 1996; Yang et al. 1996). Modeling studies suggest that the linker in FIP-$CB_{SM}$ should allow the two GFP domains to associate similarly. The modest ionic strength dependence of the FIP-$CB_{SM}$ emission spectrum measured in the absence of calmodulin may reflect the presence of stabilizing electrostatic interactions between amino acids at the interface between the two GFP domains. Perhaps because of changes in the orientation between the two GFP domains, the efficiency of FRET between the fluorophores in FIP-$CB_{SM}$ appears to depend upon the length of the linker sequence. The $F_{440}/F_{505}$ ratio increases from a value of 0.6 with the 26 amino acid linker in FIP-$CB_{SM}$, to 0.9 and 1.5 with 20 and 11 amino acid linkers, respectively. As seen in the crystal structure, the two chromophores in a GFP dimer are ~25 Å apart (Yang et al. 1996). The complex between $(Ca^{2+})_4$-calmodulin and the smooth muscle myosin light chain kinase calmodulin-binding domain forms a globular structure 40 Å in diameter (Crivici and Ikura 1995). When calmodulin binds to the kinase calmodulin-binding domain in the FIP-$CB_{SM}$ linker, it adopts an α-helical conformation. In this conformation the 17 residue sequence has a length of ~30 Å, about half its length in an extended conformation. Thus, when $(Ca^{2+})_4$-calmodulin is bound to the linker in FIP-$CB_{SM}$, the distance between the fluorophores is likely to increase from ~25 Å to ~65 Å, with calmodulin tightly sandwiched between the two GFP domains (FIG. 1). The efficiency of FRET depends upon the distance between the donor and acceptor fluorophores and upon the relative orientation of their dipole moments (Stryer 1978). Changes in the distance and possibly also the orientation parameters is clearly the basis for the observed calmodulin-dependent change in the FIP-$CB_{SM}$ fluorescence emission spectrum. In attempting to design FIPs with novel specificities, it is important to bear in mind that shortening of the linker sequence in FIP-$CB_{SM}$ when $(Ca^{2+})_4$-calmodulin is bound may paradoxically help to force the GFP domains apart.

Purified FIP-$CB_{SM}$ has been microinjected into HEK-293 cells stably transfected with epitope-tagged thyrotropin releasing hormone (TRH) receptor, a $Ca^{2+}$-mobilizing G-protein-coupled receptor (Nelson and Hinkle 1994). The response of the FIP-$CB_{SM}$ in these cells to externally applied TRH, ionomycin and 1,2-bis (o-aminophenoxy)ethane-N,N, N',N'-tetraacetic acid (BAPTA) was measured. The concentration of the FIP-$CB_{SM}$ solution used in microinjection experiments was 80 μM, and an estimate of intracellular FIP-$CB_{SM}$ is in a concentration range of 1–10 μM in microinjected cells, similar to estimates for the intracellular concentrations of high-abundance calmodulin targets, including smooth muscle myosin light chain kinase, calcineurin, calmodulindependent protein kinase II and cerebellar nitric oxide synthase (Tansey et al. 1994). When FIP-$CB_{SM}$ fluorescence is excited at 380 nm, images of whole cells using an $F_{510}$, $F_{440}$ emission ratio and time courses for relative changes in whole-cell $F_{510}$ exhibit striking responses to changes in the intracellular $Ca^{2+}$ ion concentration (FIGS. 6–11). The results suggest no discernable lag (<300 ms) between activation of TRH receptor and formation of significant levels of $(Ca^{2+})_4$-calmodulin-target complexes in the nucleus or cytoplasm (FIGS. 6–11).

Figure 6:
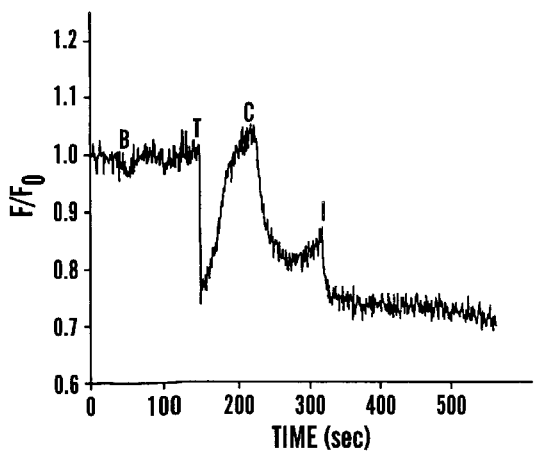
FIGS. 6–11 show time courses for area-normalized enhanced fluorescence in cells microinjected with FIP-$CB_{SM}$.
Figure 7:
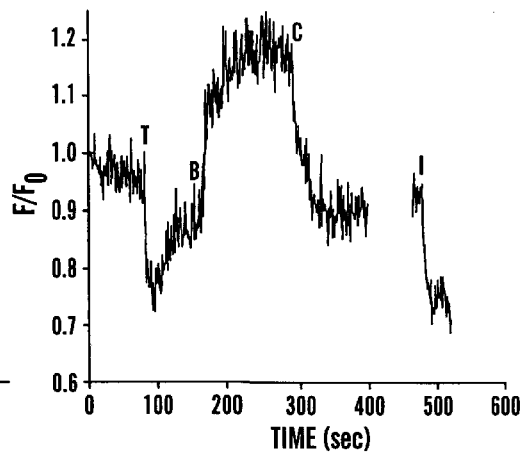
Figure 8:
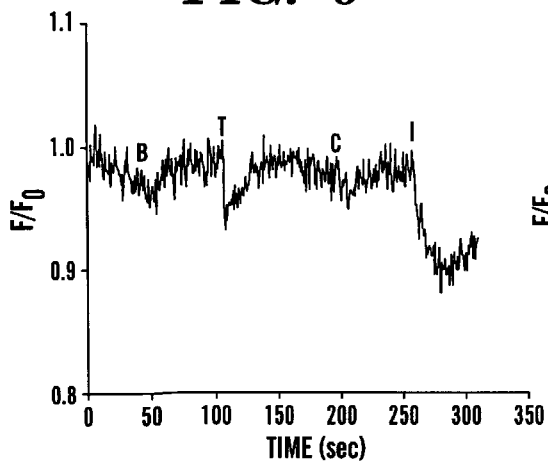
Figure 9:
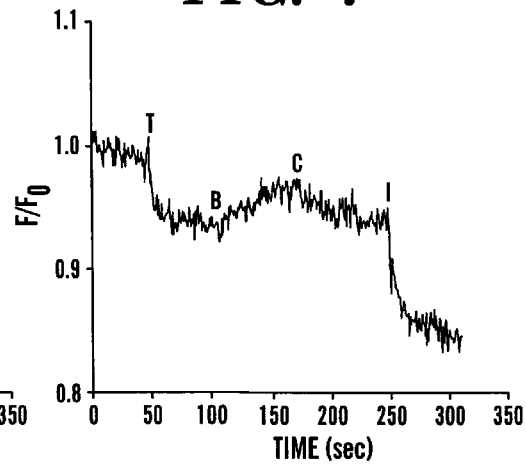

To estimate the maximal intracellular FIP-$CB_{SM}$ response, cells were injected with a 1:1 mole ratio of FIP-$CB_{SM}$ and calmodulin. In spite of the higher and more sustained $Ca^{2+}$ levels caused by ionomycin treatment, both ionomycin and TRH elicit a similar FIP-$CB_{SM}$ response in these cells, suggesting that is near the maximum (FIGS. 6 and 7). The average decrease in $F_{510}$ caused by ionomycin or TRH is ~30%. The average ionomycin-dependent decrease in $F_{510}$ seen in cells injected with FIP-$CB_{SM}$ alone is ~10% (FIGS. 7 and 8). This difference between cells injected with FIP-$CB_{SM}$ alone and those injected with FIP-$CB_{SM}$/calmodulin appears to be independent of the intracellular FIP-$CB_{SM}$ concentration as estimated from the area-normalized $F_{510}$ of resting cells, which varies by a factor of 8 among different cells. The lower FIP-$CB_{SM}$ response exhibited in cells injected with the indicator alone suggests a limiting free $(Ca^{2+})_4$-calmodulin concentration in the cell. This is also consistent with the significantly greater reduction in $F_{510}$ caused by ionomycin treatment of these cells, compared with that caused by TRH treatment, since the higher and more sustained $Ca^{2+}$ ion levels resulting from ionomycin treatment would be expected to lead to higher levels of $(Ca^{2+})_4$-calmodulin (FIGS. 6–11).

Figure 10:
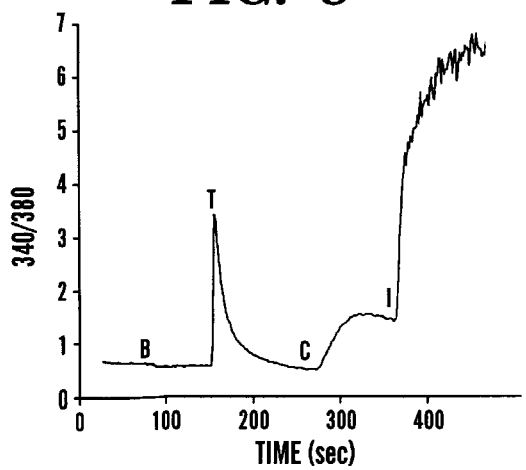
Figure 11:
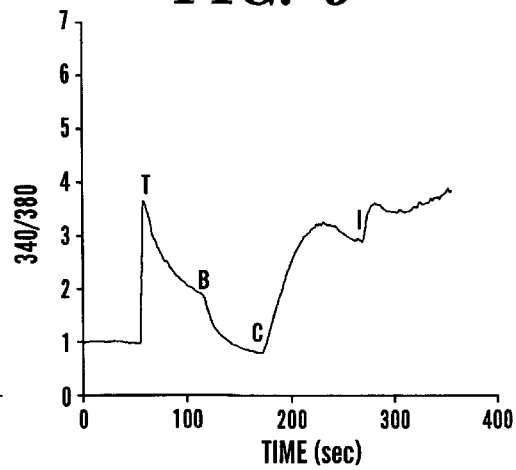

Assuming that the $F_{510}$ value measured in the presence of BAPTA represents completely unliganded FIP-$CB_{SM}$, and that $F_{510}$ value measured in ionomycin treated cells injected with FIP-$CB_{SM}$/calmodulin represents fully liganded FIP-$CB_{SM}$, then the fractional response to ionomycin seen with cells injected only with FIP-$CB_{SM}$ corresponds to a free $(Ca^{2+})_4$-calmodulin level of 0.2 nM. Treatment with BAPTA can cause $F_{510}$ in cells injected with FIP-$CB_{SM}$ or FIP-$CB_{SM}$/calmodulin to increase above the value measured at the start of the experiment (FIGS. 10 and 11). This indicates a significant basal level of $(Ca^{2+})_4$-calmodulin, which is unfortunately difficult to quantitate. However, the 30% reduction in $F_{510}$ measured in cells microinjected with FIP-$CB_{SM}$/calmodulin represents ~50% of the indicator's dynamic range, so the basal $(Ca^{2+})_4$-calmodulin concentration in cells is unlikely to exceed 0.4 nM (FIG. 2). One can therefore conservatively estimate that the average free $(Ca^{2+})_4$-calmodulin level increases to ~1 nM in microinjected cells treated with ionomycin. As with any intracellular indicator, FIP-$CB_{SM}$ undoubtedly affects homeostasis of the ligand it is designed to detect: $(Ca^{2+})_4$-calmodulin.

A low maximal level of $(Ca^{2+})_4$-calmodulin in cells is consistent with mobility studies of microinjected tagged calmodulin, which indicate that >95% of the total calmodulin is bound to other intracellular proteins at a saturating free $Ca^{2+}$ ion concentration. A low maximal level of $(Ca^{2+})_4$-calmodulin also suggests that for a typical target, with a 1 nM dissociation constant for $(Ca^{2+})_4$-calmodulin, changes in calmodulin-binding affinity will result in proportional changes in calmodulin-dependent target activity. In agreement with this, Stull et al. (1993) have demonstrated that a 10-fold decrease in the affinity of smooth muscle myosin light chain kinase for $(Ca^{2+})_4$-calmodulin significantly reduces levels of this enzyme activity in smooth muscle cells.

Cells injected cytoplasmically with FIP-$CB_{SM}$ exhibit a diffuse fluorescence that is excluded from the nucleus and other cellular organelles. Imaging using the $F_{510}/F_{440}$ ratio shows an obvious $Ca^{2+}$-dependent FIP-$CB_{SM}$ response in cells injected either with the FIP-$CB_{SM}$ alone or with FIP-$CB_{SM}$/calmodulin. A clear FIP-$CB_{SM}$ response is observed in both cytoplasm and nucleus. It has been suggested that calmodulin plays an important role in controlling events in the nucleus, including mitosis (Lu et al. 1993; Wang et al. 1996). The results certainly indicate that comparable levels of free $(Ca^{2+})_4$-calmodulin are achieved in the nucleus and cytosol. There appear to be regional variations in the FIP-$CB_{SM}$ response that may represent a heterogeneous distribution of calmodulin and/or free $Ca^{2+}$ ion in the cell.

EXAMPLE II

FIG. 2 shows the calmodulin-dependent changes in the FIP-$CB_{SM}$ fluorescence emission spectrum FIP-$CB_{SM}$ at a concentration of 1 $\mu$M was titrated with 0.2 $\mu$M increments of calmodulin in the presence of 300 $\mu$M $CaCl_2$. The buffer also contained 25 mM Tris-HCl, pH 7.5 and 0.1 M NaCl. Fluorescence was excited at 380 nm. The effects of calmodulin on the FIP-$CB_{SM}$ emission spectra are completely reversed by 5 mM EDTA. A scheme depicting the conformational change undergone by FIP-$CB_{SM}$ upon binding $(Ca^{2+})_4$-calmodulin is presented in FIG. 1. The RGFP (R) and BGFP (B) domains in FIP-$CB_{SM}$ are joined by the linker sequence: SEQ ID NO:1: GTSSRRKWNKTGHAVRAIGRLSSTGA, which contains the calmodulin-binding domain from avian smooth muscle myosin light chain kinase (Guerriero et al. 1986), shown in boldface type. The fluorophores in the GFP domains are represented by shaded rectangles. The shape used for the GFP domains is based upon the published crystal structures for GFP, which indicate an eleven-stranded β-barrel (Ormo et al. 1996; Yang et al. 1996). Based upon the corresponding calmodulin-peptide structure, the linker sequence in FIP-$CB_{SM}$ is enfolded by the two lobes of $(Ca^{2+})_4$-calmodulin and adopts an α-helical conformation. Calmodulin is depicted as two hemispheres, corresponding to the lobes, joined by the flexible central helix tether (Persechini and Kretsinger 1988). The two $Ca^{2+}$ ions bound to each lobe in $(Ca^{2+})_4$-calmodulin are depicted as filled circles. FIP-$CB_{SM}$ was expressed in *E. coli* and purified essentially as described by Mitra et al. (1996). The purified protein exhibits optical absorbance maxima at 480 and 380 nm with respective $\epsilon$ values of 89 and 36 $mM^{-1}cm^{-1}$, which correspond with the absorbances of RGFP and BGFP, respectively. The 380 nm-excited fluorescence emission spectrum of a control protein in which the linker sequence used in FIP-$CB_{SM}$ is replaced by the sequence: SEQ ID NO:2: GTSSGSSTTGA is unaffected by $(Ca^{2+})_4$-calmodulin levels as high as 3 $\mu$M. The FIP-$CB_{SM}$ emission spectrum is independent of pH between 7.0 and 8.0, either in the presence or absence of bound calmodulin. The emission spectrum of FIP-$CB_{SM}$ is affected by changes in ionic strength; the $F_{440}/F_{505}$ emission ratio increases by 0.1 with each 50 mM increment in ionic strength between 130 and 300 mM. In the presence of a saturating level of $(Ca^{2+})_4$-calmodulin the $F_{440}/F_{505}$ ratio of FIP-$CB_{SM}$ is unaffected by ionic strength changes in this range.

EXAMPLE III

FIGS. 3–5 show the characterization of calmodulin binding by FIP-$CB_{SM}$. FIG. 3 shows the titration of a mixture of 8.2 nM FIP-$CB_{SM}$ and 200 nM calmodulin with increasing concentrations of free $Ca^{2+}$ ion. Free $Ca^{2+}$ ion concentrations were established by incremental additions of standard $CaCl_2$ solutions to a buffer containing 50 mM Tris-HCl, pH 8.0, 0.1 M NaCl, 0.5 mM $MgCl_2$, and 3 mM 1,2-bis(o-amino-5-5'-dibromophenoxy) ethane-N,N,N',N'-tetraacetic acid ($Br_2$BAPTA) at 25° C. Values for the free $Ca^{2+}$ concentration given in the figure were calculated using the MaxChelator software package (Bers et al. 1994). The curve shown in the figure was calculated using an equation of the form: $F=\alpha(L^n)/(L^n+K_a)$ where F is the fractional saturation of FIP-$CB_{SM}$ with calmodulin, given in the figure as $1-[(F-F_{min})/(F_{max}-F_{min})]$, L is the free $Ca^{2+}$ ligand concentration, $K_a$ is an apparent dissociation constant that depends upon the total amount of calmodulin, and n is the number of interacting sites, which equaled 3.9 for the curve shown. This indicates that $(Ca^{2+})_4$-calmodulin is the species bound by FIP-$CB_{SM}$. F is the fluorescence measured at 505 nm, $F_{max}$ and $F_{min}$ are the values for F measured at maximal and minimal free $Ca^{2+}$ ion concentrations. α is a correction factor allowing adjustment of the maximal fraction of FIP-$CB_{SM}$ bound to give the best fit. α values are <1.1 for the curves shown in panels A and B.

FIG. 4 shows the binding of $(Ca^{2+})_4$-calmodulin to FIP-$CB_{SM}$ at concentrations of 1(■) and 1.4 (▲) nM. Buffer conditions are described above for FIG. 2 (Example II). The curve fitting data measured at a 1 nM FIP-$CB_{SM}$ concentration was generated according to a standard single-site kinetic model. The curve fitting data measured at a 1.4 nM FIP-$CB_{SM}$ concentration was generated according to an equation of the form: $F=\alpha\{(P_t+L_t+K_d) -[(P_t+L_t+K_d)^2 -4(P_t)(L_t)]^{0.5}\}/2(P_t)$, where $L_t$ is the total calmodulin concentration and $P_t$ is the total FIP-$CB_{SM}$ concentration. In both cases the curves fitting the data were generated using a $K_d$ value of 0.4 nM. Emission spectra for titration of FIP-$CB_{SM}$ at a 1.4 nM concentration are shown in FIG. 5.

EXAMPLE IV

FIGS. 6–11 show time courses for area-normalized enhanced fluorescence in cells microinjected with FIP-$CB_{SM}$. FIP-$CB_{SM}$ fluorescence was excited at 380 nm and measured at 510 nm. Data are presented as simple fraction of the $F_{510}$ measured at the start of the experiment ($F_0$), except for fura-2 measurements, which are presented as 340/380 fluorescence excitation ratios, determined as previously described. All traces are averages of data collected from 8–15 cells. B, T, C and I indicate external applications of 3 mM BAPTA, 1 µM TRH, 3 mM $CaCl_2$ and 3 µM ionomycin. FIGS. 6 and 7 contain traces for cells injected with FIP-$CB_{SM}$ and calmodulin in a 1:1 mole ratio. Traces for cells injected with FIP-$CB_{SM}$ alone are presented in FIGS. 8 and 9. FIGS. 10 and 11 contain traces for the fura-2 response of mock-injected cells. It was found that microinjection of a synthetic peptide based on the calmodulin-binding domain in skeletal muscle myosin light chain kinase (Blumenthal and Krebs 1987) at a concentration identical to that used for FIP-$CB_{SM}$ has no discernable effect on the fura-2 response. This was also found to be the case for cells microinjected with concentrations of calmodulin comparable to those co-injected with FIP-$CB_{SM}$. Cells microinjected with a control GFP fusion protein (see above description of FIG. 2; Example II), either alone or in a 1:1 mole ratio with calmodulin, exhibited no significant $Ca^{2+}$-dependent changes in F510. The gap in the trace presented in FIG. 7 is due to a camera malfunction.

EXAMPLE V

Figure 12:
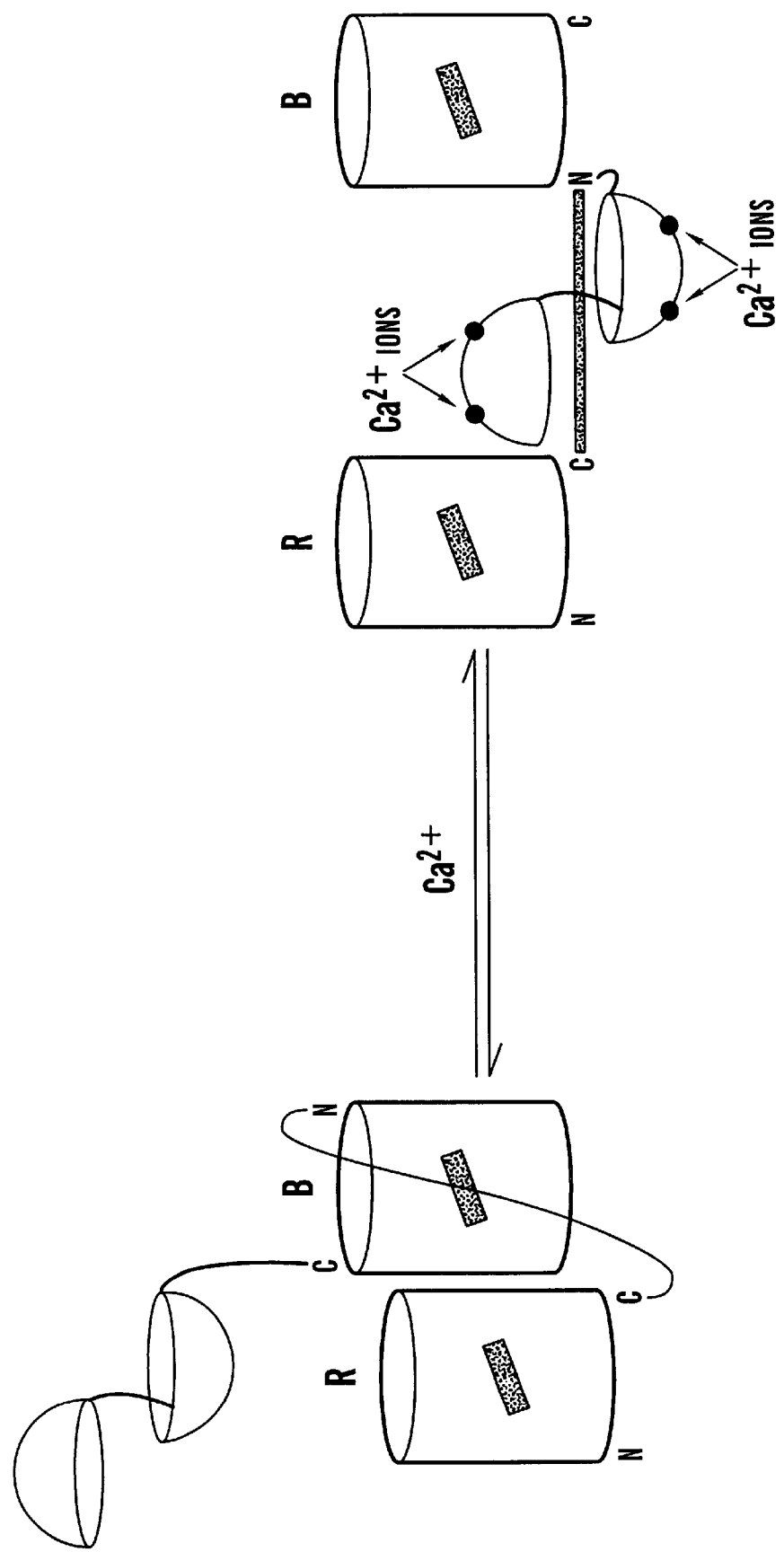
FIG. 12 illustrates the conformational change undergone by FIP-$CA_3$ upon binding $Ca^{2+}$.

A second fluorescent indicator protein (FIP-$CA_3$) useful for monitoring levels of secondary ligands is shown in FIG. 12. In this embodiment, the calmodulin protein (the primary ligand) is covalently attached to the green fluorescent protein complex described in the above examples. FRET in this embodiment is dependent only on $Ca^{2+}$ (a secondary ligand) levels.

Figure 13:
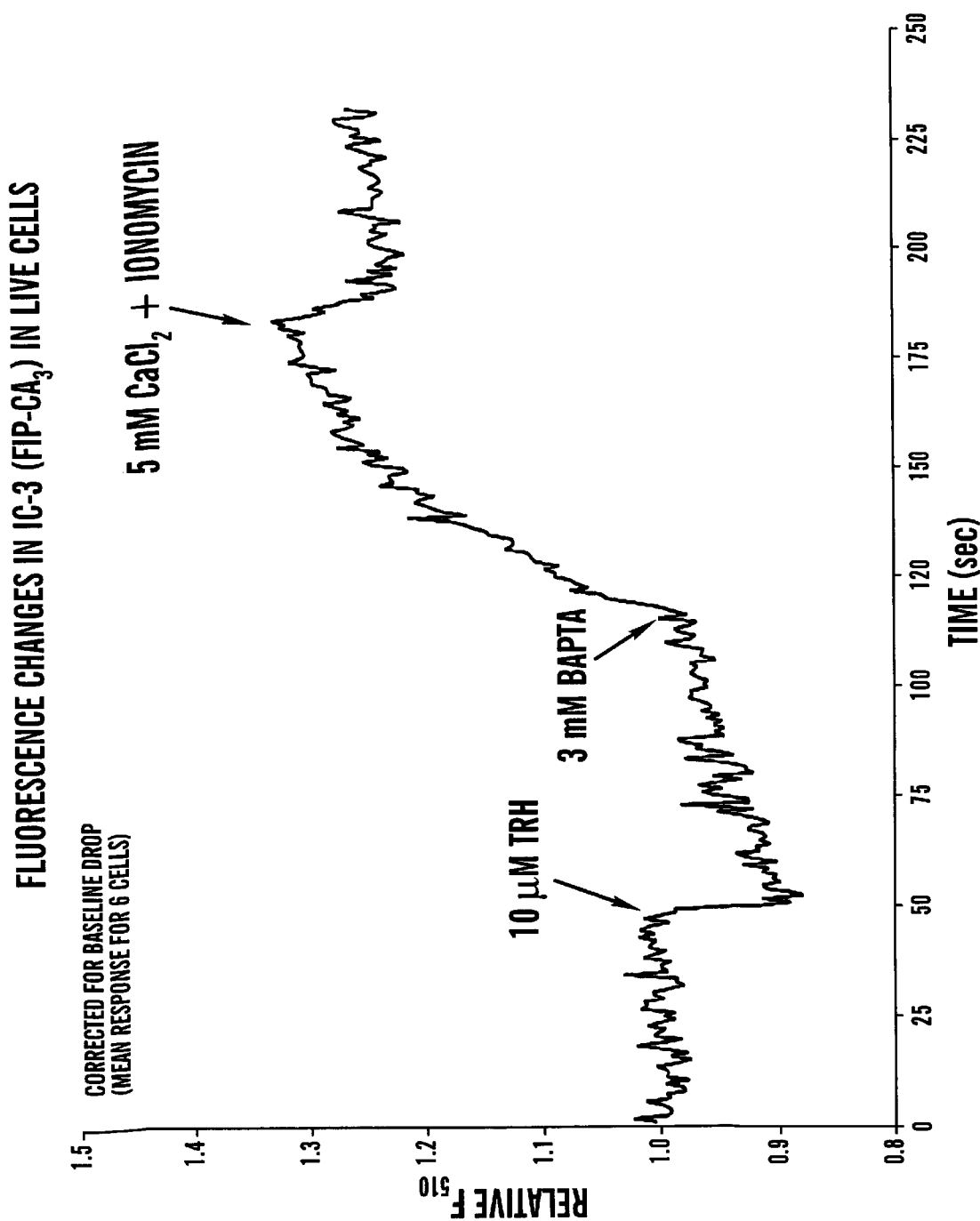
FIG. 13 shows a time course for area-normalized enhanced fluorescence in cells microinjected with FIP-$CA_3$.

FIG. 13 shows the time course for area-normalized enhanced fluorescence in cells microinjected with FIP-$CA_3$ (comparable to FIGS. 6–11 for FIP-$CB_{SM}$).

Figure 14:
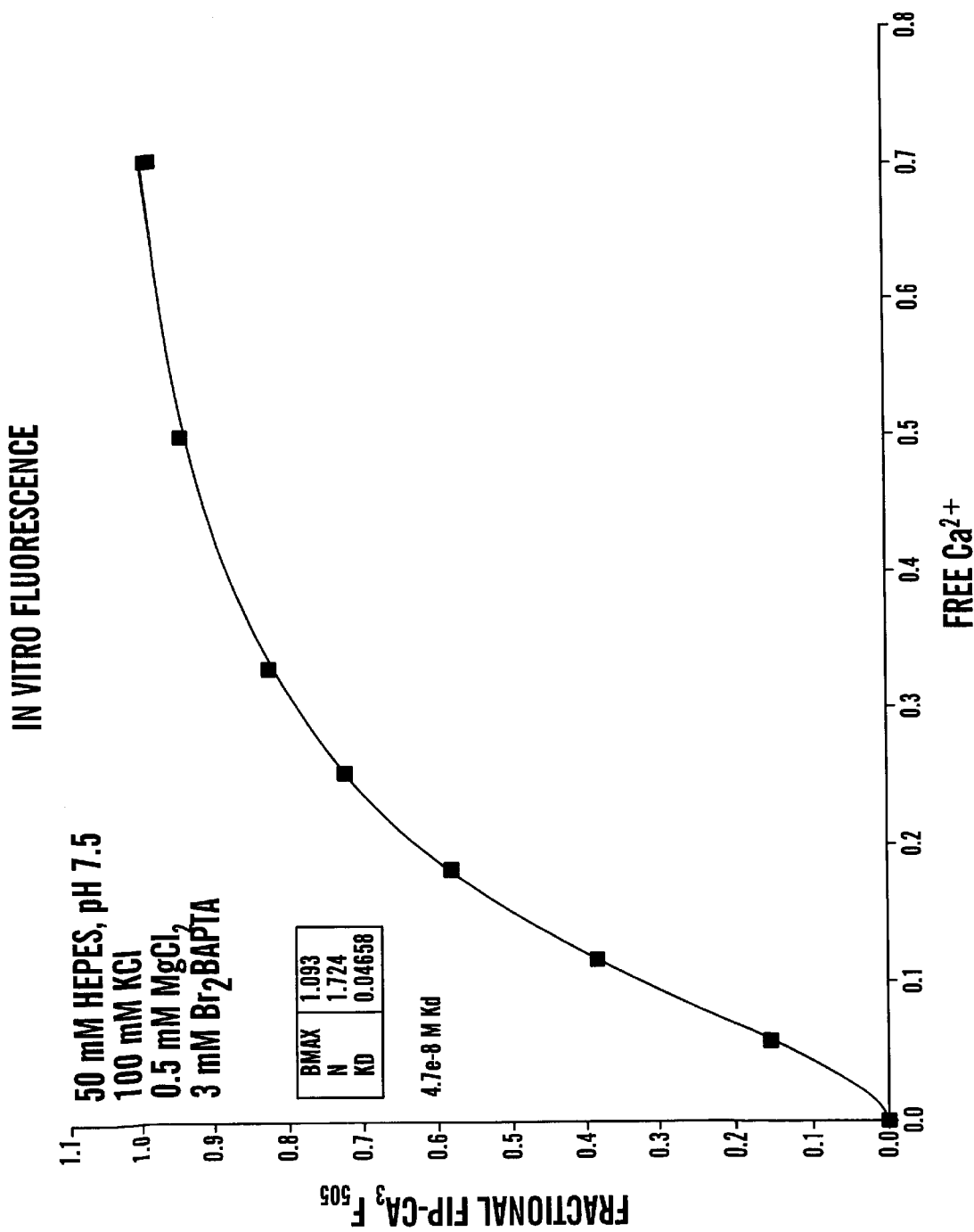
FIG. 14 characterizes the calcium binding by FIP-$CA_3$, showing the titration of FIP-$CA_3$ with increasing concentrations of free $Ca^{2+}$ ion.

FIG. 14 characterizes the calcium binding by FIP-$CA_3$, showing the titration of FIP-$CA_3$ with increasing concentrations of free $Ca^{2+}$ ion.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Primary Sequences of some known and putative calmodulin binding domains of protein and peptide calmodulin targets

| Target[a] | Sequence[b] (with SEQ ID NO: in parentheses) | Reference |
|---|---|---|
| skMLCK (M13) (c) | K R R W K K N F I A V S A A N R F K K I S S S G A L (3)(SEQ ID NO:3) | Blumenthal et al. 1987 |
| smMLCK (smMLCKp) | A R R K W Q K T G H A V R A I G R L S S (4)SEQ ID NO:4 | Lowenstein et al. 1992 |
| CaMKII | A R R K L K G A I L T T M L A T R N F S (5)SEQ ID NO:5 | Novack et al. 1991 |
| Caldesmon | G V R N I K S M W E K G N V A S S (6)SEQ ID NO:6 | Zhang et al. 1994 |
| Calspermin | A R R K L K A A V K A V V A S S R L G S (7)SEQ ID NO:7 | Payne et al. 1988 |
| PFK (M11) | F M N N W E V Y K L L A H I R P P A P K S G S Y T V (8)SEQ ID NO:8 | Buschmeier et al. 1987 |
| Calcineurin | A R K E V I R N K I R A I G K M A R V F S V L R (9)SEQ ID NO:9 | Kincaid et al. 1988 |
| PhK (PhK5) | L R R L I D A Y A F R I Y G H W V K K G Q Q Q N R G (10)SEQ ID NO:10 | Dasgupta et al. 1989 |
| (PhK13) | R G F K K L S V R I Y Y Q Y R R V K P G (11)SEQ ID NO:11 | Dasgupta et al. 1989 |
| Ca$^{2+}$-ATPase (C28W) | L R R G Q I L W F R G L N R I Q T Q I K V N K V Q L E K (12)SEQ ID NO:12 | Vorherr et al. 1990 |
| 59-kDa PDE | R R K K M W Q R L K G I L R C L V K Q L E K (13)SEQ ID NO:13 | Vorherr et al. 1993 |
| 60-kDa PDE | T E K M W Q R L L K G I L R C L V K Q L E K (14)SEQ ID NO:14 | Novack et al. 1991 |
| NOS (NO-30) | K R R A I G F K K L A E A V K F S A K L M G Q (15)SEQ ID NO:15 | Vorherr et al. 1993 |
| Type I AC (AC-28) | I K P A K R M K F K T V C Y L L V Q L M H C R K M F K A (16)SEQ ID NO:16 | Vorherr et al. 1993 |
| Bordetella pertussis AC | I D L L W K K I A R A G A R S A V G T E A (17)SEQ ID NO:17 | Oldenburg et al. 1992 |
| Neuromodulin | K A H K A A T K I Q A S F R G H I T R K K L K G E K K (18)SEQ ID NO:18 | Chapman et al. 1991 |
| Spectrin | K T A S P W K S A R L M V H T V A T F N S I K E (19)SEQ ID NO:19 | Leto et al. 1989 |
| MARCKS | K K K K K R F S F K K S F K L S G F S F K K N R K (20)SEQ ID NO:20 | Graff et al. 1991 |
| F52 or MacMARCKS | K K K K K R F S F K K P F K L S G L S F K R N R K (21)SEQ ID NO:21 | Blackshear et al. 1992 |
| β-Adducin | K Q Q K E K T R W L N T P N T Y L R V N V A D E V Q R N M G S (22)SEQ ID NO:22 | Scaramuzzino 1993 |
| HSP90α | K D Q V A N S A F Q E R L R K H G L E V I (23)SEQ ID NO:23 | Minami et al. 1993 |
| HIV-1 gp160 | Y H R L R D L L L I V K R I V E L L G R R (24)SEQ ID NO:24 | Srinivas et al. 1993 |
| BBMHCI | Q Q L A T L I Q K T Y R G W R C R T H Y Q L M (25)SEQ ID NO:25 | Mercer et al. 1991 |
| Dilute MHC | R A A C I R I Q K T I R G W L L R K K R Y L C M Q (26)SEQ ID NO:26 | Mercer et al. 1991 |
| Mastoparan | I N L K A L A A L A K K I L (27)SEQ ID NO:27 | |
| Melittin | G I G A V L K V L T T G L P A L I S W I K R K R Q Q (28)SEQ ID NO:28 | Malencik et al. 1983b |
| Glucagon | H S Q G T F T T S D Y S K Y L D S R R A Q D F V Q W L M N T (29)SEQ ID NO:29 | Malencik et al. 1983b |
| Secretin | H S D G T F T S E L S R L R D S A R L Q R L L Q G L V (30)SEQ ID NO:30 | Malencik et al. 1983a |
| VIP | H S D A V F T D N Y T R L R K Q M A V K K Y L N S I L N (31)SEQ ID NO:31 | Malencik et al. 1983a |
| GIP | Y A D G T F I S D Y S A I M N K I R Q Q D F V N W L L A Q Q K S (32)SEQ ID NO:32 | Malencik et al. 1983a |
| Model peptide CBP2 | K L W K K L L K L L K K L L K L G (33)SEQ ID NO:33 | DeGrado et al. 1985 |

[a]Abbreviations: AC, adenylyl cyclase; BBMHCI, brush-border myosin heavy chain-I; CaMKII, calmodulin kinase II; CBP2, calmodulin binding peptide-2; GIP, gastrin inhibitory peptide; HIV-1 gp160, human immunodeficiency virus envelope glycoprotein 160; HSP, heat-shock protein; MARCKS, myristoylated alanine-rich C kinase substrate; MHC, myosin heavy chain; NOS, nitric oxide synthase; PDE, phosphodiesterase; PFK, phosphofructokinase; PhK, phosphorylase kinase; sk-, smMLCK, skeletal muscle- and smooth muscle-myosin light chain kinase; VIP, vasoactive intestinal peptide.
[b]Alignment of the CaM domains was made by visual inspection based on alignment of the putatively conserved major (bold and underlined) and minor (bold) hydrophobic anchors that interact with the hydrophobic patches of the C- and N-terminal domains of CaM (Ikura et al. 1992), and on the alignment of the conserved basic residue (bold and Italicized) analogous to that residue of MLCK that is required for activation by CaM (Meador et al. 1992; Meador et al. 1993). Precise boundaries of the CaM-binding domain are not known for all targets.
[c]Names in parentheses are those used in the literature for the synthetic peptides containing the sequences listed.

LIST OF REFERENCES CITED

Adelstein, R. S., and Klee, C. B., *Journal of Biological Chemistry*, 256:7501 (1981).
Bers, D., et al., in *A practical guide to the study of calcium in living cells*, Nuccitelli, R., Ed., Vol. 40, pp. 3, Academic Press, New York (1994).
Blackshear, P. J., et al., J Biol Chem 267:13540 (1992).
Blumenthal, D. K., and Krebs, E. G., *Meth. Enzymol.*, 139:115 (1987).
Bredt, D. S., and Snyder, S. H., Proc Natl Acad Sci USA 87:682 (1990)
Buschmeier, B., et al., J Biol Chem 262:9454 (1987).
Chapman, E. R., et al., J Biol Chem 266:207 (1991).
Cho, H. J., et al., J Exp Med 176:599 (1992).
Crameri, A., et al., Nature Biotechnology 14:315–319 (1996).
Crivici, A., and Ikura, M., *Annual Review of Biophysics & Biomolecular Structure*, 24:85–116 (1995).
Dasgupta, M., et al., J Biol Chem 264:17156 (1989).
DeGrado, W. F., et al., J Cell Biochem 29:83 (1985).
Delegrave, S., et al., *Biotechnology* 13:151–154 (1995).
Edelman, A. M., et al., Journal of Biological Chemistry 271:10806 (1996).
Graff, J. M., et al., J Biol Chem 266:14390 (1991).
Guerriero, V., et al., *Biochemistry*, 25:8372 (1986).
Gura, T., *Science* 273:1336 (1996).
Heim, R., et al., *Proceedings of the National Academy of Sciences of the United States of America*, 91:12501 (1994).
Ikura, M., et al., Science 256:632 (1992).
Inouye, S. and Tsuji, F. I., *FEBS Letters* 341:277–280 (1994).
Kincaid, R. L., et al., Proc Natl Acad Sci USA 85:8983 (1988).
Kink, J. A., et al., Cell 62:165 (1990).
Leto, T. L., et al., J Biol Chem 264:5826 (1989).
Lowenstein, C. J., and Snyder, S. H., Cell 70:705 (1992).
Lu, K. P., and Means, A. R., *Endocrine Rev.*, 14:40 (1993).
Malencik, D. A., and Anderson, S. R., Biochemistry 22:1995 (1983a).
Malencik, D. A., and Anderson, S. R., Biochem Biophys Res Commun 114:50 (1983b).
Manalan, A. S., and Klee, C. B., Adv Cycl Nuc Prot Phos Res 18:227 (1984).
Marshall, J., et al., *Neuron* 14:211–215 (1995).
Meador, W. E., et al., Science 257:1251 (1992).
Meador, W. E., et al., Nature 262:1718 (1993).
Means, A. R., et al., Pharmacology & Therapeutics 50:255 (1991).
Mercer, J. A., et al., Nature 349:709 (1991).
Minami, Y., et al., J Biol Chem 268:9604 (1993).
Mitra, R. D., et al., *Gene*, 173:13–17 (1996).
Nelson, E. J., and Hinkle, P. M., *Endocrinology*, 135:1084 (1994).
Novack, J. P., et al., Biochemistry 30:7940 (1991).
Oldenburg, D. J., et al., Biochemistry 31:8884 (1992).
Ormo, M., et al., *Science* 273:1392–1395 (1996).
Payne, M. E., et al., J Biol Chem 263:7190 (1988).
Persechini, A., and Kretsinger, R. H., *Journal of Biological Chemistry*, 263:12175 (1988).
Persechini, A., et al., Journal of Biological Chemistry 271:62–67 (1996).
Scaramuzzino, D. A., and Morrow, J. S., Proc Natl Acad Sci USA 90:3398 (1993).
Srinivas, S. K., et al., J Biol Chem 268:22895 (1993).
Stryer, L., *Annual Review of Biochemistry*, 47:819 (1978).
Stull, J. T., et al., *Molecular & Cellular Biochemistry*, 127:229 (1993).
Tansey, M. G., et al., *Journal of Biological Chemistry*, 269:9912 (1994).
Vorherr, T., et al., Biochemistry 29:355 (1990).
Vorherr, T., et al., Biochemistry 32:6081 (1993).
Wang, J. H., et al., *Biochimica et Biophysica Acta—Molecular Cell Research*, 1313:223 (1996).
Yang, F., et al., *Nature Biotechnology*, 14:1246–1251 (1996).
Youvan, D. C. and Michel-Beyerle, M. E., Nature Biotechnology 14:1219–1220 (1996).
Zhang, M., et al., Biochemistry 33:1163 (1994).

---

What is claimed is:

1. A method of monitoring a change in the amount of calmodulin associated with metal ion in a cell, said method comprising:
   exposing a cell to a first wavelength, wherein the cell contains metal ions and a green fluorescent protein complex comprising:
      a first green fluorescent protein which is excited at the first wavelength and which emits fluorescence at a second wavelength;
      a calmodulin-binding peptide capable of reversibly binding to calmodulin associated with metal ion, the calmodulin-binding peptide having amino terminal and carboxy terminal ends, one of the amino terminal and carboxy terminal ends of the calmodulin-binding peptide being covalently attached to the first green fluorescent protein; and
      a second green fluorescent protein which is excited at the second wavelength and which emits fluorescence at a third wavelength, the other of the amino terminal and carboxy terminal ends of the calmodulin-binding peptide being covalently attached to the second green fluorescent protein;
   measuring a base amount of fluorescence emission at the third wavelength when the cell is exposed to the first wavelength;
   measuring a second amount of fluorescence emission at the third wavelength when the cell is exposed to the first wavelength, said measuring the second amount of fluorescence emission being carried out subsequent to said measuring the base amount of fluorescence emission; and
   comparing the second amount of fluorescence emission to the base amount of fluorescence emission, wherein a lesser second amount of fluorescence emission indicates an increase in the amount of calmodulin associated with metal ion in the cell and a greater second amount of fluorescence emission indicates a decrease in the amount of calmodulin associated with metal ion in the cell.

2. The method of claim 1 wherein the calmodulin-binding peptide has an amino acid sequence as shown in SEQ ID No: 1.

3. The method of claim 1 wherein the first green fluorescent protein is a blue-shifted green fluorescent protein.

4. The method of claim 3 wherein the blue-shifted green fluorescent protein is excited at a wavelength maxima of 380 nm and emits fluorescence at a wavelength maxima of 440 nm.

5. The method of claim 1 wherein the second green fluorescent protein is a red-shifted green fluorescent protein.

6. The method of claim 5 wherein the red-shifted green fluorescent protein is excited at a wavelength maxima of 495 nm and emits fluorescence at a wavelength maxima of 505 nm.

7. The method of claim 1 wherein the metal ion is selected from the group consisting of calcium manganese, nickel, and cadmium.

8. The method of claim 7 wherein the metal ion is calcium.

9. A green fluorescent protein complex comprising:
   a first green fluorescent protein which is excited at a first wavelength and which emits fluorescence at a second wavelength;
   a calmodulin-binding peptide which reversibly binds calmodulin associated with metal ion, said calmodulin-binding peptide having amino terminal and carboxy terminal ends, one of the amino terminal and carboxy terminal ends of said calmodulin-binding peptide being covalently attached to said first green fluorescent protein; and
   a second green fluorescent protein which is excited at said second wavelength and which emits fluorescence at a third wavelength, the other of the amino terminal and carboxy terminal ends of said calmodulin-binding peptide being covalently attached to said second green fluorescent protein,
      wherein when said green fluorescent protein complex is excited at said first wavelength, the amount of fluorescence emission at said third wavelength is reduced when said calmodulin-binding peptide is bound reversibly to calmodulin associated with metal ion as compared to the amount of fluorescence emission at said third wavelength when said calmodulin-binding peptide is not bound to calmodulin associated with metal ion.

10. The green fluorescent protein complex of claim 9 wherein said calmodulin-binding peptide has an amino acid sequence as shown in SEQ ID No: 1.

11. The green fluorescent protein complex of claim 9 wherein said first green fluorescent protein is a blue-shifted green fluorescent protein.

12. The green fluorescent protein complex of claim 11 wherein said blue-shifted green fluorescent protein is excited at a wavelength maxima of 380 nm and emits fluorescence at a wavelength maxima of 440 nm.

13. The green fluorescent protein complex of claim 9 wherein said second green fluorescent protein is a red-shifted green fluorescent protein.

14. The green fluorescent protein complex of claim 13 wherein said red-shifted green fluorescent protein is excited at a wavelength maxima of 495 nm and emits fluorescence at a wavelength maxima of 505 nm.

15. The green fluorescent protein complex of claim 9 further comprising calmodulin covalently attached to one of the other components of said green fluorescent protein complex.

16. A cell comprising the green fluorescent protein complex of claim 9.

17. The green fluorescent protein complex of claim 15, wherein said one of the other components of said green fluorescent protein complex is either said first green fluorescent protein or said second green fluorescent protein.

18. The green fluorescent protein complex according to claim 9, wherein the one end of said calmodulin-binding peptide is the amino terminal end and the other end of said calmodulin-binding peptide is the carboxy terminal end.

19. The method of claim 1, wherein the one end of the calmodulin-binding peptide is the amino terminal end and the other end of the calmodulin-binding peptide is the carboxy terminal end.

20. A method of monitoring a change in the amount of metal ions in a cell, said method comprising:
   exposing a cell to a first wavelength, wherein the cell contains a green fluorescent protein complex according to claim 9 and calmodulin;
   measuring a base amount of fluorescence emission at the third wavelength when the cell is exposed to the first wavelength;
   measuring a second amount of fluorescence emission at the third wavelength when the cell is exposed to the first wavelength, said measuring the second amount of fluorescence emission being carried out subsequent to said measuring the base amount of fluorescence emission; and
   comparing the second amount of fluorescence emission to the base amount of fluorescence emission, wherein a lesser second amount of fluorescence emission indicates an increase in the amount of metal ions in the cell and a greater second amount of fluorescence emission indicates a decrease in the amount of metal ions in the cell.

21. The method of claim 20 wherein calmodulin is covalently attached to one of the other components of the green fluorescent protein complex.

22. The method of claim 21, wherein the one of the other components of the green fluorescent protein complex is either the first green fluorescent protein or the second green fluorescent protein.

23. The method of claim 20 wherein the calmodulin-binding peptide has an amino acid sequence corresponding to SEQ. ID. No. 1.

24. The method of claim 20 wherein the metal ion is selected from a group consisting of calcium, manganese, nickel, and cadmium ions.

25. The method of claim 24 wherein the metal ion is a calcium ion.

26. The method of claim 20 wherein the first green fluorescent protein is a blue-shifted green fluorescent protein.

27. The method of claim 26 wherein the blue-shifted green fluorescent protein is excited at a wavelength maxima of 380 nm and emits fluorescence at a wavelength maxima of 440 nm.

28. The method of claim 20 wherein the second green fluorescent protein is a red-shifted green fluorescent protein.

29. The method of claim 28 wherein the red-shifted green fluorescent protein is excited at a wavelength maxima of 495 nm and emits fluorescence at a wavelength maxima of 505 nm.

30. A method of monitoring a change in the amount of calmodulin associated with metal ion in a cell, said method comprising:
   exposing a cell to a first wavelength, wherein the cell contains metal ions and a green fluorescent protein complex comprising:
      a first green fluorescent protein which is excited at the first wavelength and which emits fluorescence at a second wavelength and a third wavelength;
      a calmodulin-binding peptide capable of reversibly binding to calmodulin associated with metal ion, the calmodulin-binding peptide having amino terminal and carboxy terminal ends, one of the amino terminal and carboxy terminal ends of the calmodulin-binding peptide being covalently attached to the first green fluorescent protein; and a second green fluorescent protein which is excited at the third wavelength and which emits fluorescence at a fourth wavelength, the other of the amino terminal and carboxy terminal ends of the calmodulin-binding peptide being covalently attached to the second green fluorescent protein;

measuring a base amount of fluorescence emission at the fourth wavelength or the second wavelength when the cell is exposed to the first wavelength;

measuring a second amount of fluorescence emission at the fourth wavelength or the second wavelength when the cell is exposed to the first wavelength, said measuring the second amount of fluorescence emission being carried out subsequent to said measuring the base amount of fluorescence emission; and comparing the second amount of fluorescence emission to the base amount of fluorescence emission for either the second wavelength or the fourth wavelength, wherein a greater second amount of fluorescence emission at the second wavelength or a lesser second amount of fluorescence emission at the fourth wavelength indicates an increase in the amount of calmodulin associated with metal ion in the cell and wherein a lesser second amount of fluorescence emission at the second wavelength or a greater second amount of fluorescence emission at the fourth wavelength indicates a decrease in the amount of calmodulin associated with metal ion in the cell.

31. The method according to claim 30, wherein said measuring the base amount of fluorescence emission is carried out for fluorescence emissions at the second wavelength and fluorescence emissions at the fourth wavelength, wherein said measuring the second amount of fluorescence emission is carried out for fluorescence emissions at the second wavelength and fluorescence emissions at the fourth wavelength, and wherein said comparing is carried out for fluorescence emissions at the second wavelength and fluorescence emissions at the fourth wavelength.

32. The method according to claim 31, wherein said comparing further comprises:

calculating an emission ratio for the base amount or the second amount of fluorescence emissions, the emission ratio being a ratio of the fluorescence emissions at the fourth wavelength and the fluorescence emissions at the second wavelength.

33. A method of quantitating the free concentration in a cell of calmodulin associated with a metal ion, said method comprising:

exposing a cell to a first wavelength, wherein the cell contains metal ions and a green fluorescent protein complex comprising:

a first green fluorescent protein which is excited at the first wavelength and which emits fluorescence at a second wavelength and a third wavelength;

a calmodulin-binding peptide capable of reversibly binding to calmodulin associated with metal ion, the calmodulin-binding peptide having amino terminal and carboxy terminal ends, one of the amino terminal and carboxy terminal ends of the calmodulin-binding peptide being covalently attached to the first green fluorescent protein; and a second green fluorescent protein which is excited at the third wavelength and which emits fluorescence at a fourth wavelength, the other of the amino terminal and carboxy terminal ends of the calmodulin-binding peptide being covalently attached to the second green fluorescent protein;

first measuring a maximum amount of fluorescence emission at the fourth wavelength or a minimum amount of fluorescence emission at the second wavelength under conditions when substantially no metal ion associates with calmodulin and the cell is exposed to the first wavelength;

second measuring a minimum amount of fluorescence emission at the fourth wavelength or a maximum amount of fluorescence emission at the second wavelength under conditions when the calmodulin-binding peptide in substantially all the green fluorescence protein complexes in the cell binds to calmodulin associated with metal ion and the cell is exposed to the first wavelength;

third measuring a third amount of fluorescence emission at the fourth wavelength or the second wavelength when the cell is exposed to the first wavelength; and calculating the free concentration of calmodulin associated with metal ion present in the cell during said third measuring by comparing the third amount of fluorescence emission to the maximum amount of fluorescence emission and the minimum amount of fluorescence emission at the second wavelength or the fourth wavelength.

* * * * *